US010729555B1

(12) United States Patent
Rappaport et al.

(10) Patent No.: US 10,729,555 B1
(45) Date of Patent: Aug. 4, 2020

(54) IMPLANTABLE SPINAL SUPPORT STRUCTURE AND METHOD

(71) Applicant: Presidio Surgical, Inc., Alamo, CA (US)

(72) Inventors: James R. Rappaport, Reno, NV (US); David A. Poirier, Alamo, CA (US)

(73) Assignee: Presidio Surgical, Inc., Alamo, CA (US)

( * ) Notice: Subject to any disclaimer, the term of this patent is extended or adjusted under 35 U.S.C. 154(b) by 13 days.

(21) Appl. No.: 15/798,114

(22) Filed: Oct. 30, 2017

(51) Int. Cl.
*A61F 2/44* (2006.01)
*A61F 2/30* (2006.01)
*A61B 17/16* (2006.01)
*A61B 17/17* (2006.01)

(52) U.S. Cl.
CPC ........ *A61F 2/4465* (2013.01); *A61F 2/30767* (2013.01); *A61B 17/1637* (2013.01); *A61B 17/1655* (2013.01); *A61B 17/1671* (2013.01); *A61B 17/1757* (2013.01); *A61F 2002/30405* (2013.01); *A61F 2002/30777* (2013.01); *A61F 2002/30785* (2013.01); *A61F 2002/30851* (2013.01)

(58) Field of Classification Search
CPC .................................................... A61F 2/4465
See application file for complete search history.

(56) References Cited

U.S. PATENT DOCUMENTS

| 6,056,749 A * | 5/2000 | Kuslich ............. A61B 17/1757 606/86 A |
| 6,224,631 B1 * | 5/2001 | Kohrs .................. A61F 2/4611 623/17.11 |
| 6,428,575 B2 * | 8/2002 | Koo ....................... A61F 2/446 623/17.11 |
| 2004/0073216 A1 * | 4/2004 | Lieberman ............ A61F 2/4455 606/279 |
| 2004/0230305 A1 * | 11/2004 | Gorensek ................ A61F 2/446 623/17.11 |
| 2007/0156241 A1 * | 7/2007 | Reiley ................ A61B 17/1615 623/17.11 |

* cited by examiner

*Primary Examiner* — Olivia C Chang
(74) *Attorney, Agent, or Firm* — Heisler & Associates

(57) ABSTRACT

A beam acts as an implantable spinal support structure. The beam is generally cylindrical in form with two semi-cylindrical shells defining a cylindrical contour of the beam and with a web passing through a central axis of the beam and joining midpoints of the two shells together. The shells preferably have threads on an outer surface thereof to engage bone within a cylindrical hole passing through two adjacent vertebrae spanning a disk space, for support of the vertebrae such as for fusion thereof together. One end of the beam can be tapered to maximize structural support for the vertebrae. This tapered end can be provided as a separate extension removably attachable to other portions of the beam in one embodiment. A method for implantation is also disclosed where the beam is implanted at an angle to the spinal axis and intersecting a disk space between adjacent vertebrae.

20 Claims, 5 Drawing Sheets

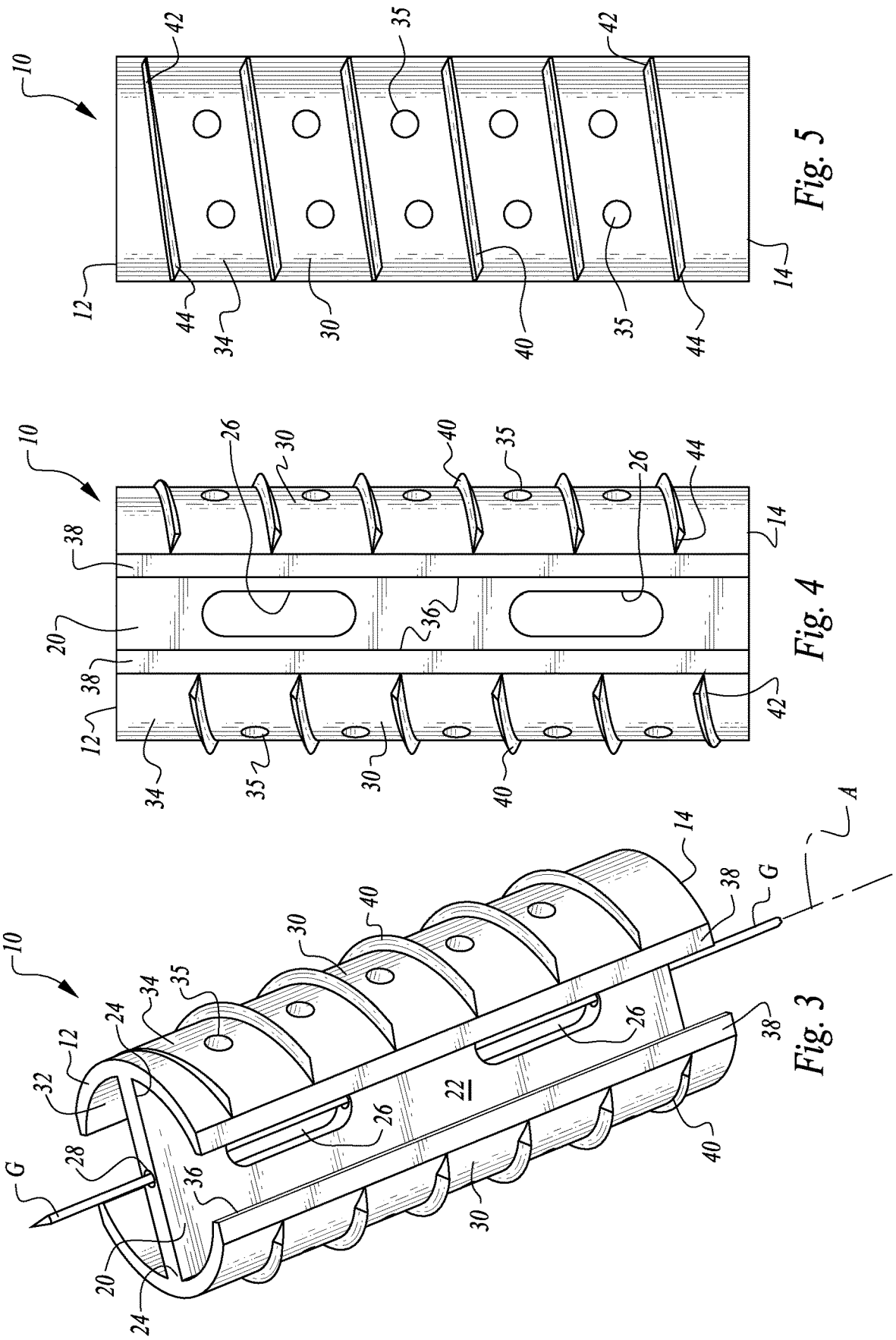

IMPLANTABLE SPINAL SUPPORT STRUCTURE AND METHOD

FIELD OF THE INVENTION

The following invention relates to implantable medical devices for implantation within and across an intervertebral disk space between adjacent vertebrae to support the spine while fusing adjacent vertebrae together. More particularly, this invention relates to an implantable spinal support structure which spans both a disk space and portions of vertebrae above and below the disk space internally and which is optimized for strength.

BACKGROUND OF THE INVENTION

The spine carries very high vertical loads within the body with a structure made up of a series of individual vertebrae spaced apart by intervertebral disks therebetween. The vertebrae are rigid in form while the disks exhibit a certain degree of flexibility and elasticity.

A common spinal failure involves failure or fracture of the pars interarticularis. The resulting spinal displacement, called spondylolisthesis, typically causes extreme pain and in some cases other neurologic and health problems.

A common treatment for such spondylolisthesis is for the disk to be removed and for the two vertebrae on either side of the intervertebral disk space to be fused together. Such a spinal fusion procedure first involves removal of the disk from the intervertebral disk space. Next, some form of structure is placed between the vertebrae and within the disk space to distract the two vertebrae away from each other; pedicle screws and rods are then inserted to hold the vertebrae in place. Finally, bone in-growth media is placed around this implant, to cause bone to grow between the two vertebrae and through the disk space, causing the two vertebrae to fuse together. The implant holds the vertebrae in place until the new bone has formed to fuse the vertebrae together. Once fusion is complete, new bone material within the disk space takes over the load carrying function within the disk space, with the implant remaining and providing some additional stability to the spine.

Typically, the implant placed within the disk space does not couple the two vertebrae together, but rather only fills the disk space and distracts the two vertebrae away from each other. The vertebrae are held adjacent to each other by pedicle screws and other bodily structures which remain in place to hold the adjacent vertebrae together.

The combination of intervertebral disk space implants, also commonly referred to as "cages" and the use of spinal stabilization rods and pedicle screws is effective in many cases for supporting adjacent vertebrae during spinal fusion. However, in other cases the degree of stabilization is insufficient and the spinal fusion procedure is less than completely successful, leaving the patient with ongoing pain and loss of function.

The degree of success of such prior art spinal fusion procedures varies to some degree depending on where along the spine the fusion is to take place. One portion of the spine where prior art cages, spinal rods and pedicle screws have been particularly ineffective is at the disk space between the sacrum and the lumbar vertebra adjacent the sacrum, often referred to as the L5 vertebra. The way that the sacrum angles away from a centerline of the spine makes it difficult for the implantation of spinal rods and cages, particularly in the setting of spondylolisthesis, and even if implanted, the angle makes it difficult for the forces involved to be effectively supported by such prior art vertebrae stabilization implants. Accordingly a need exists for a spinal stabilization implant which is particularly effective in holding the sacrum and the L5 vertebra fixed together while fusion takes place across the disk space therebetween.

One family of prior art implants that is known for stabilizing the lumbar vertebra and the sacrum are described in U.S. Pat. Nos. 6,558,386; 6,899,716; 6,921,403; 7,087,058; and 7,309,338. These implants require an elaborate caudal approach to the lower spine.

Spondylolisthesis occurs when two adjacent vertebrae become displaced in an anterior or posterior direction relative to each other. Spondylolisthesis can occur to varying degrees with the degree of severity corresponding with the need for repair by fusing the vertebrae together. A need exists for an implant which can secure the L5 vertebrae to the sacrum (or other two adjacent vertebrae) sufficiently that spondylolisthesis can be treated through spinal fusion effectively, simply and with a minimum of implants and with either an anterior or posterior approach.

SUMMARY OF THE INVENTION

With this invention in at least one embodiment, an implant is provided which spans an intervertebral disk space and passes through one vertebra adjacent the disk space and at least into a second vertebra on an opposite side of the disk space. The implant structure is generally in the form of an elongate beam with a circular cross-section. A hole is first formed transverse to the disk space, passing through a first vertebra adjacent the disk space, spanning the disk space and extending at least partially into a second vertebra adjacent the disk space and opposite the first vertebra. This hole is generally cylindrical in form and transverse to the disk space. A centerline of this hole is aligned with a vertical central plane bisecting the spine, but is skewed relative to both a centerline of the spine and a plane in which the disk space is oriented. The hole thus passes somewhat diagonally. Most preferably in one embodiment, this angle matches generally an angle that the sacrum exhibits relative to the spine, so that the hole can extend into the sacrum. The sacrum is in the form of the second vertebra adjacent the disk space. The implant is formed to be generally cylindrical with a shape matching that of the hole so that it can be placed into the hole and spanning the disk space, while also joining the two adjacent vertebrae together.

Preferably, the implant is in the form of a beam having a web and a pair of shells on opposite sides of the web. The web is preferably substantially planar and the shells are preferably semi-circular in cross-section and forming portions of a generally cylindrical contour for the overall beam. The shells are spaced apart at peripheral edges thereof by gaps. When the beam support structure is implanted, the web is preferably oriented in a vertical plane with the web extending both vertically and in a posterior and anterior direction so that the web follows a plane which bisects the spine. Such an orientation provides maximum strength for supporting the spine loads adjacent the disk space.

The shells preferably include threads on outer surfaces thereof. These threads are sized and shaped to engage bone adjacent the hole passing through the disk space and adjacent vertebrae. The hole can be tapped with female threads if desired in advance, or the threads on the beam can be self-tapping. Thus, the beam is advanced by rotation, with the threads engaging the bone and drawing the beam structure into the hole for implantation. The threads are preferably designed to harvest small amounts of bone to function as a self-grafting implant. The shells also preferably include holes passing therethrough to facilitate bony in-growth and thru-growth around and through the beam to thoroughly fuse the adjacent vertebrae and beam together.

In a first exemplary embodiment, the beam is shown with ends which are perpendicular to a central axis of the beam. In a second exemplary embodiment a trailing end of the beam is provided with a tapered end to add additional material for maximum strength to be imparted from the beam structure to the adjacent vertebra. In a third exemplary embodiment, the beam structure is in the form of a two part beam with a first part having ends which are perpendicular to the central axis of the beam structure and a second part in the form of an extension which has one end which is perpendicular to the central axis and a second end which tapers relative to the central axis. This extension is threadably attachable to an end of the extendible beam to customize a length of the overall extendible beam and to facilitate proper orientation of the tapered end of the extension. Such a configuration minimizes the inventory of implants required to fit all potential patient anatomies.

A method for implanting the beam structure according to one embodiment can be followed which involves first gaining access to an implantation site, typically on an anterior exterior surface of the L5 vertebrae and at an angle of approximately 45° to the vertical. Typically, a guide wire is next fed through the L5 vertebrae, across the disk space and into the proximal end of the sacrum until the guide wire is positioned along a desired centerline for the beam implant. The guide wire can be guided through the use of fluoroscopy to provide it precisely where desired. After the guide wire has been placed where desired and its position verified, a drill or other hole forming tool, of either a hand or powered variety which is cannulated can be utilized on the guide wire to form the hole. Typically, instruments for use in forming this hole, as well as the guide wire, can be advanced either through a cannula either endoscopically or semi-laproscopically (also referred to as a mini-laparatomy) to minimize the invasiveness of the procedure and attendant decrease in complications and recovery time for the patient.

After the hole has been formed along the guide wire, typically a very tip of the guide wire remains embedded within the sacrum. A tapping tool can be utilized if desired to tap female threads into bony structures on an inside cylindrical wall of the hole formed in the L5 vertebra and the sacrum. Alternatively, a self-tapping series of threads can be provided on the beam implant to form the threads as the beam is advanced into the hole. The web of the beam implant structure preferably includes a bore passing therethrough which can receive the guide wire. Thus, the beam can be advanced along the guide wire and into the hole with the guide wire helping to guide and stabilize the beam as it is advanced into the hole. Such advancement typically occurs by rotation and with threads on an outer surface of the beam engaging the bone and drawing the beam into the hole.

If the beam has a tapered end, it is typically advanced axially as far as desired and until the web is oriented in the plane desired for final positioning of the beam. Finally, the guide wire is removed and bone in-growth media is placed surrounding the beam. Typically, during formation of the hole and tapping of the threads, bone that is removed is scavenged for use in enhancing the bone in-growth process, with such bone fragments being both biocompatible for the patient and improving the quality of fusion between the two adjacent vertebrae.

While this procedure involves spanning the disk space, it could take place after a diskectomy procedure where the intervertebral disk is removed, or can merely take place through the disk space and leave portions of the disk (such as the annulus) in place.

If the beam is in the form of a two-part extendible beam after the primary beam structure has been implanted, an extension is then selected to have a desired height from a set of extensions having different heights in the form of lengths along a central axis thereof. The extension, which preferably also has a bore passing through a web thereof, is then advanced on the guide wire to the trailing end of the beam where it can be threaded directly into the trailing end of the beam. The extension is then rotated until it has been fully attached to the beam and with the web of the extension aligned with the web of the beam. The set of extensions can also provide various different taper angles to select from.

OBJECTS OF THE INVENTION

Accordingly, a primary object of the present invention is to provide an implant for stabilization of vertebrae adjacent a disk space during a spinal fusion procedure.

Another object of the present invention is to provide an implant for stabilizing the L5 vertebrae and the sacrum together during fusion thereof.

Another object of the present invention is to provide an intervertebral space implant which extends into vertebrae adjacent the disk space for secure stabilization of the two vertebrae to each other.

Another object of the present invention is to provide an implant for use in stabilizing the vertebrae adjacent the sacrum for treatment of spondylolisthesis.

Another object of the present invention is to provide a method for implanting a beam structure to affix the L5 vertebrae to the sacrum for fusion thereof.

Another object of the present invention is to provide a method for secure fixation of two adjacent vertebrae together.

Another object of the present invention is to provide an implant design for spinal fusion which entails a minimum of inventory.

Another object of the present invention is to provide a spinal fusion implant which can be implanted with either an anterior or posterior approach.

Another object of the present invention is to be able to distract or compress across the disk space through variable thread pitches on the implant.

Other further objects of the present invention will become apparent from a careful reading of the included drawing figures, the claims and detailed description of the invention.

BRIEF DESCRIPTION OF THE DRAWINGS

FIG. 3 is a perspective view of the beam implant of this invention according to a first embodiment.

FIG. 4 is a side elevation view of that which is shown in FIG. 3.

FIG. 5 is a front elevation view of that which is shown in FIG. 3.

DESCRIPTION OF THE PREFERRED EMBODIMENT

Figure 2:
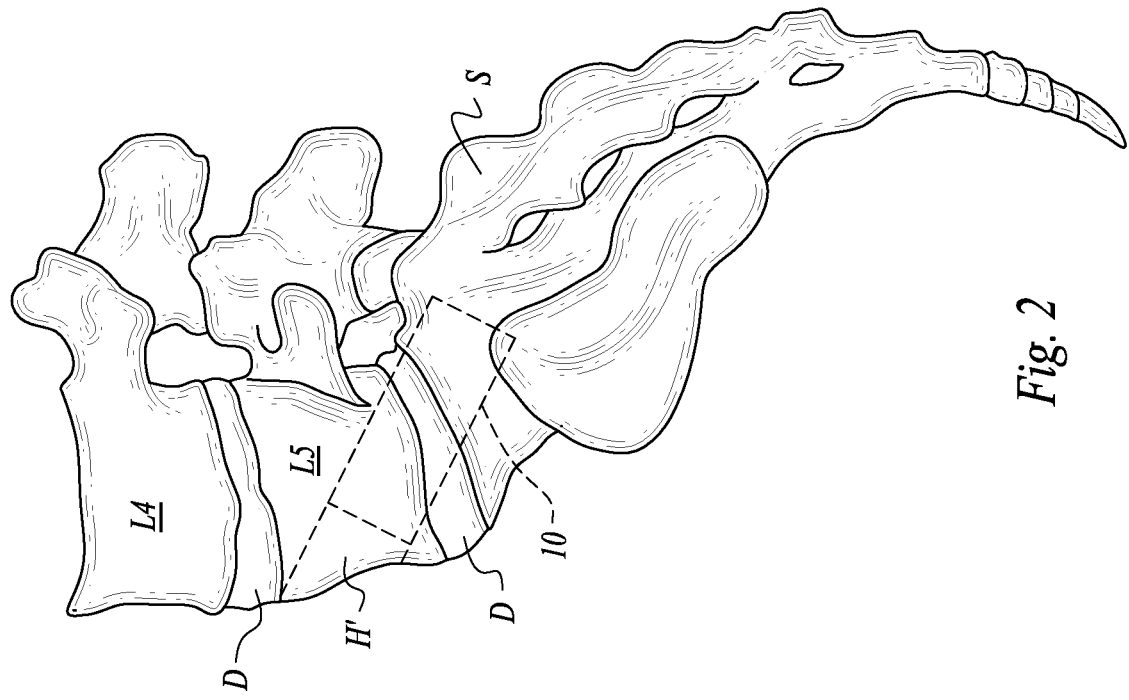
FIG. 2 is a side elevation view of that which is shown in FIG. 1 for illustrating one position for the beam implant structure of this invention.

Referring to the drawings, wherein like reference numerals represent like parts throughout the various drawing figures, reference numeral 10 is directed to a beam (FIG. 3) defining a first embodiment of an implant according to this invention for fixing adjacent vertebrae together within the spine. The implant beam 10 is well suited for fixation of the sacrum S (FIGS. 1 and 2) to the L5 vertebra to affix the L5 vertebra to the sacrum, such as in the treatment of spondylolisthesis. The implant can have ends which are perpendicular to a centerline of the beam 10 (FIGS. 1-8) or can have a tapered end (FIGS. 9-11), and the tapered end can be a permanent portion of the tapered beam 110 or be formed as a separate extension 250 attachable to an extendible beam 210. The beam 10, 110, 210 exhibits a web 20 and shell 30 configuration to exhibit both high strength and a degree of bone in-growth to maximize the strength of the fused joint between the vertebrae adjacent the disk space D, such as fixation of the L5 vertebra to the sacrum S.

In essence, and with particular reference to FIGS. 3-5, basic details of the beam 10 are described according to a first embodiment. The beam 10 has an elongate form between a leading end 12 and a trailing end 14. A web 20 extends from the leading end 12 to the trailing end 14. The web 20 is preferably substantially planar and generally rectangular in form. A bore can be provided longitudinally between side surfaces 22 of the web 20 for receipt of a guide wire G passing therethrough. Shells 30 are joined to opposite long edges of the web 20. The shells 30 are semi-circular in cross-section and semi-cylindrical in form, spaced from each other by gaps that keep the shells 30 from forming a complete cylinder surrounding a centerline of the beam 10. Threads 40 are preferably formed on an outer wall 34 of the shells 30. These threads 40 have a common pitch on each of the shells 30 and are spaced so that the threads 40 can advance the beam 10 by rotation into a cylindrical hole formed in vertebrae to be fused together and with the threads 40 additionally helping to keep the beam 10 securely in its implanted position. Holes 35 preferably pass through the shells 30 through which bone in-growth can occur to secure the beam 10 most fully to the vertebrae adjacent the disk space after fusion of the vertebrae together.

In an alternative tapered beam 110 embodiment (FIGS. 10 and 11) one of the ends, typically the trailing end, has the form of a tapered end 120 which is angled away from perpendicular to the central axis A of the tapered beam 110, by an angle, such as 45°. In another embodiment shown in FIGS. 12 and 13, an extendible beam 210 is provided which has a removably attachable extension 250. The extension 250 is selected having a desired length, and optionally also various different tapered end angles. This extension 250 is then threadably attached to the extendible beam 210 to form the completed beam with a tapered end that is of customizable length and taper angle.

More specifically, and with particular reference to FIGS. 3-5, particular details of the web 20 of the beam 10 are described. The web 20 acts to join the two shells 30 of the beam 10 together. The web 20 keeps the shells 30 rigidly attached together and maintains the shells 30 in position where they can provide maximum resistance to bending loads, and particularly bending loads which are generally within a vertical plane bisecting the spine.

The web 20 is preferably formed along with the shells 30 as a unitary mass of material, typically formed from a high strength biocompatible material such as titanium or an appropriate alloy of titanium such as nickel titanium. As another alternative, the web 20 and other portions of the beam 10 could be formed of stainless steel or some other biocompatible material having sufficient strength.

The web 20 has side surfaces 22 which are planar and oriented opposite each other, with a distance between the side surfaces 22 defining a thickness of the web 20. The web 20 extends laterally to junctions 24 where the web 20 is joined to the shells 30. This junction 24 could be an attachment joint, but most preferably merely defines a location where the monolithic material forming the beam 10 transitions from the web 20 to the shells 30.

Preferably, apertures 26 extend through the side surfaces 22 and define voids passing through the web 20. These apertures 26 are provided to facilitate bone in-growth during fusion, and help to fix the beam 10 to associated bone after such fusion has taken place.

A bore 28 preferably passes through the web 20 along the central axis A with a size to accommodate a guide wire G passing therethrough. This bore 28 preferably has a diameter slightly less than a thickness of the web 20 so that the bore 28 only is exposed at the ends 12, 14 of the beam 10, and through the apertures 26. If necessary, the web 28 can be thickened somewhat adjacent the bore 28 to appropriately strengthen the web 20 adjacent the bore 28. The bore 28 could be dispensed with if the beam 10 is implanted in a manner other than along a guide wire G.

With continuing reference to FIGS. 3-5, details of the shells 30 of the beam 10 are described. The shells 30 are preferably rigid semi-cylindrical structures having a semi-circular cross-section and formed along with the web 20 to define the beam 10. The shells 30 are each preferably identical in form and spaced from each other by gaps at a perimeter of the shells 30. The shells 30 together define a partial cylindrical form for the beam 10.

The shells 30 include an inner wall 32 facing inwardly toward the web 20 with portions of the inner wall 32 joined to the web 20 at the junctions 24. The shells 30 have an outer wall 34 spaced from the inner wall 32 by a thickness of the shells 30. This thickness of the shells 30 can be similar to that of the thickness of the web 20. Holes 35 preferably extend from the inner wall 32 to the outer wall 34 completely penetrating the shells 30. These holes 35 provide space through which bony in-growth can occur during spinal fusion to secure the beam 10 to adjacent vertebrae.

Each of the shells 30 extend circumferentially about the central axis A until they terminate at tips 36. These tips 36 preferably have a taper 38 on at least one side thereof so that they become narrower as they approach the tip 36. Such a taper 38 helps to assist the shells 30 in rotating into a cylindrical hole H without the tips 36 otherwise providing a point of abutment or catching upon anomalies in the cylindrical form of the hole H, and allow the beam 10 to easily advance into the cylindrical hole H formed in the vertebrae and spanning the disk space for implantation of the beam 10.

Threads 40 are preferably formed on the outer wall 34 of the shells 30. Each of these threads 40 extends from an origin 42 adjacent one of the tips 36 along a helical path to a terminus 44 adjacent an opposite one of the tips 36. The threads 40 have a slight pitch as they extend from the origin 42 to the terminus 44. This pitch is preferably standard in direction so that clockwise rotation of the beam 10 causes the beam 10 to advance into the cylindrical hole H for implantation of the beam 10. Counterclockwise rotation would thus allow for movement of the beam 10 out of the cylindrical hole H. The threads 40 preferably have a pitch and other size characteristics which are optimized for engagement of bone, and particularly bone of the vertebrae adjacent the disk space which is spanned by the beam 10.

In a simplest form of the invention, the pitch of the threads 40 is uniform between adjacent threads on each of the shells 30. The threads end at the gaps between the shells 30 and then commence again on the other side of the gap on the opposite shell 30. Threads 40 are spaced axially on opposite shells 30 by a distance which causes the threads of the opposite shells 30 to advance along a single helical path into the same grooves previously vacated by the threads 40 of the other shell 30. For instance, if the threads 40 have a pitch of one millimeter for every 15° of rotation, and the gap between the shells 30 spans 30° about the central axis of the beam 10, then when a first thread 40 terminates at the gap on one of the shells 30, the first thread 40 on the other shell 30 begins two millimeters axially displaced from where the first thread 40 of the first shell 30 terminated. The threads 40 of the opposite shells 30 thus easily follow each other helically as the beam 10 is rotationally advanced into a cylindrical hole H.

As an alternative, the threads 40 can be provided in a non-uniform manner along each of the shells 30. In particular, the threads 40 closest to the leading end 12 could be provided with a greater pitch than threads closer to the trailing end 14. In such a configuration, when the threads closest to the leading end have advanced through a first vertebra, across the disk space and into a second vertebra, the threads 40 closest to the leading end 12 will advance more rapidly axially (along arrow A of FIG. 3) than the threads 40 closest to the trailing end 14. Such a differential between the threads 40 will tend to cause the two vertebrae on opposite sides of the disk space to be drawn together slightly, helping to more securely hold the adjacent vertebrae together.

If distraction of the vertebrae is indicated, a shallower pitch can be provided for threads 40 adjacent the leading end 12 and a steeper pitch can be provided for threads adjacent the trailing end 14, so that the vertebrae are distracted away from each other on opposite sides of the disk space. This differential can be provided in a sufficiently small amount that common female threads formed in the bone can still be utilized, or threads can only be tapped into the first vertebra and the second vertebra can be tapped in a self-tapping manner with self-tapping threads on the shells 30 of the beam 10.

If desired, the beam 10 could be provided in a manner slightly distinct from a pure cylinder. For instance, the beam 10 could be provided as having a stepped cylinder outline having a first diameter adjacent the leading end 12 and a second diameter adjacent the trailing end 14, and with a step therebetween. With such a form, typically the leading end 12 would have a smaller diameter than the trailing end 14 and the hole H in the vertebrae would similarly be stepped with a smaller diameter in the second vertebra and a greater diameter in the first vertebra. With such a stepped arrangement, a greater difference in pitch could be exhibited for threads 40 adjacent the leading end 12 than for threads 40 adjacent the trailing end 14 so that a greater amount of distraction or contraction could be provided between the adjacent vertebrae. Also, such a stepped arrangement would allow for full pre-tapping of the female threads into the bone of the vertebrae very precisely before implantation of the beam 10.

Figure 8:
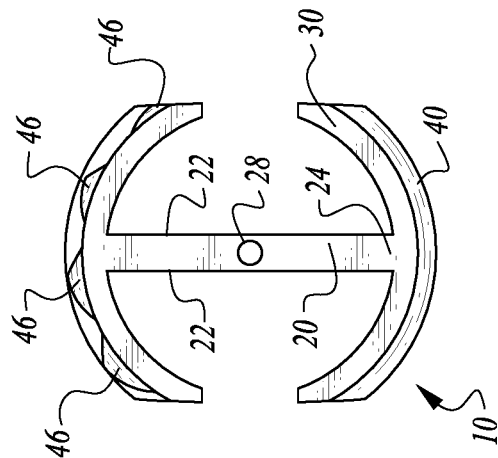
FIG. 8 is an end elevation view of that which is shown in FIG. 6.
Figure 7:
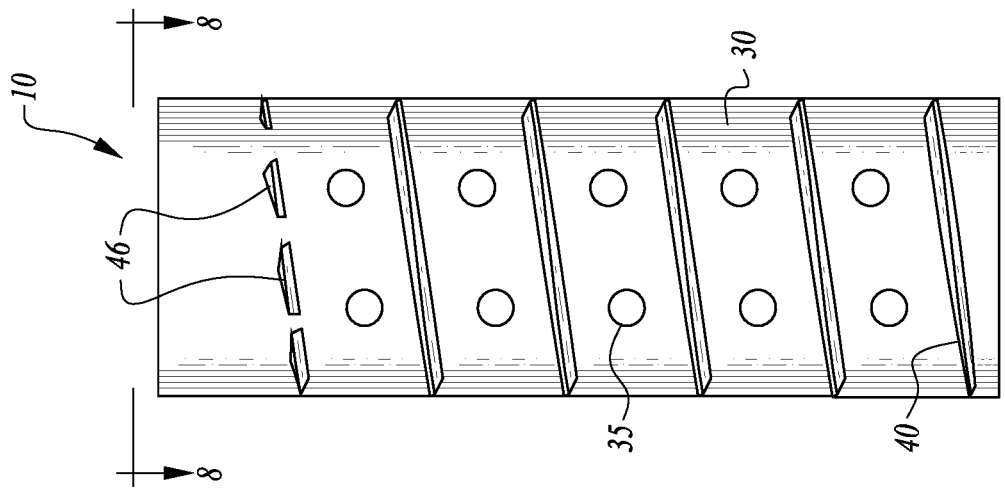
FIG. 7 is a front elevation view of that which is shown in FIG. 6.
Figure 6:
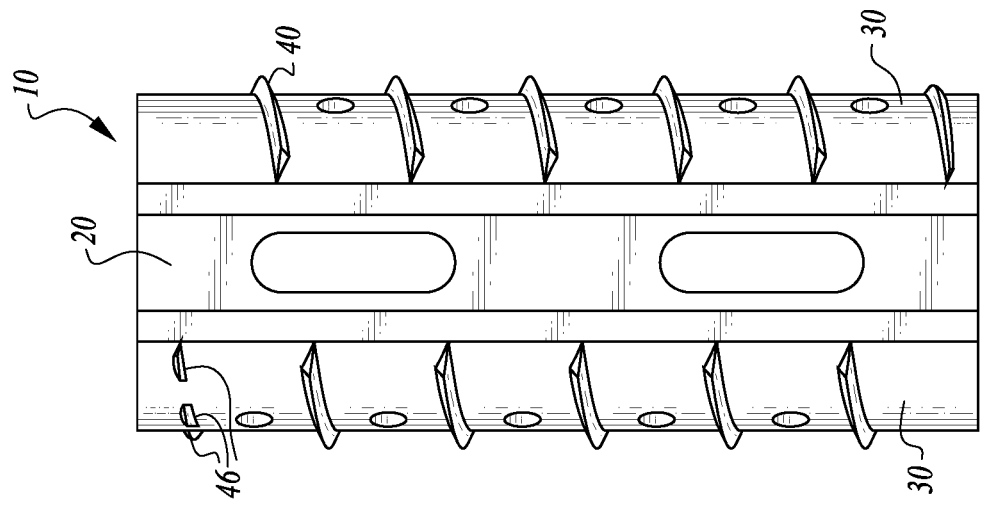
FIG. 6 is a side elevation view of a slightly modified embodiment of that which is shown in FIG. 3, which exhibits self-tapping threads.

With particular reference to FIGS. 6-8, details of an alternative embodiment of the beam 10 are provided where the threads 40 are provided of a self-tapping variety. In particular, the threads 40 are shown in this embodiment with at least a first turn of the threads 40 in the form of tapping thread teeth 46. A series of such teeth 46 are provided with each tooth 46 being successively larger. Thus, each tooth 46 cuts a small amount of bone in a groove as the beam 10 is rotated. Each tooth 46 preferably has a sharp leading edge to cut away a small portion of bone with each one of the teeth 46.

The tapping thread teeth 46 are shown with four separate tapping teeth 46 in place of a thread 40 closest to the leading end 12 of the beam 10. A greater or fewer number of teeth 46 could be provided replacing this first thread 40. Also, such tapping thread teeth 46 could be continued on the first thread 40 of the opposite shell 30 also if it is desired to take a smaller amount of bone away with each tooth 46, or if deeper female threads are to be formed in the bone. These tapping thread teeth 46 are preferably only provided on the leading end 12 of the beam 10. The beam 10 could be configured to be reversible and with such tapping thread teeth 46 on both the thread 40 closest to the leading end 12 and the thread 40 closest to the trailing end 14.

As an alternative, various different forms of tapping teeth could be provided to configure the beam 10 to be self-tapping. For instance, rather than tapping teeth, threads could merely be provided which start out with a lesser major diameter closer to the leading end 12, and with successive threads further from the leading diameter 12 having a slightly greater major diameter, such that each thread extends slightly more deeply into the bone adjacent the cylindrical hole into which the beam 10 is to be implanted. The threads could be formed sufficiently rough to grind away bone as they advance.

Figures 9, 10, 11:
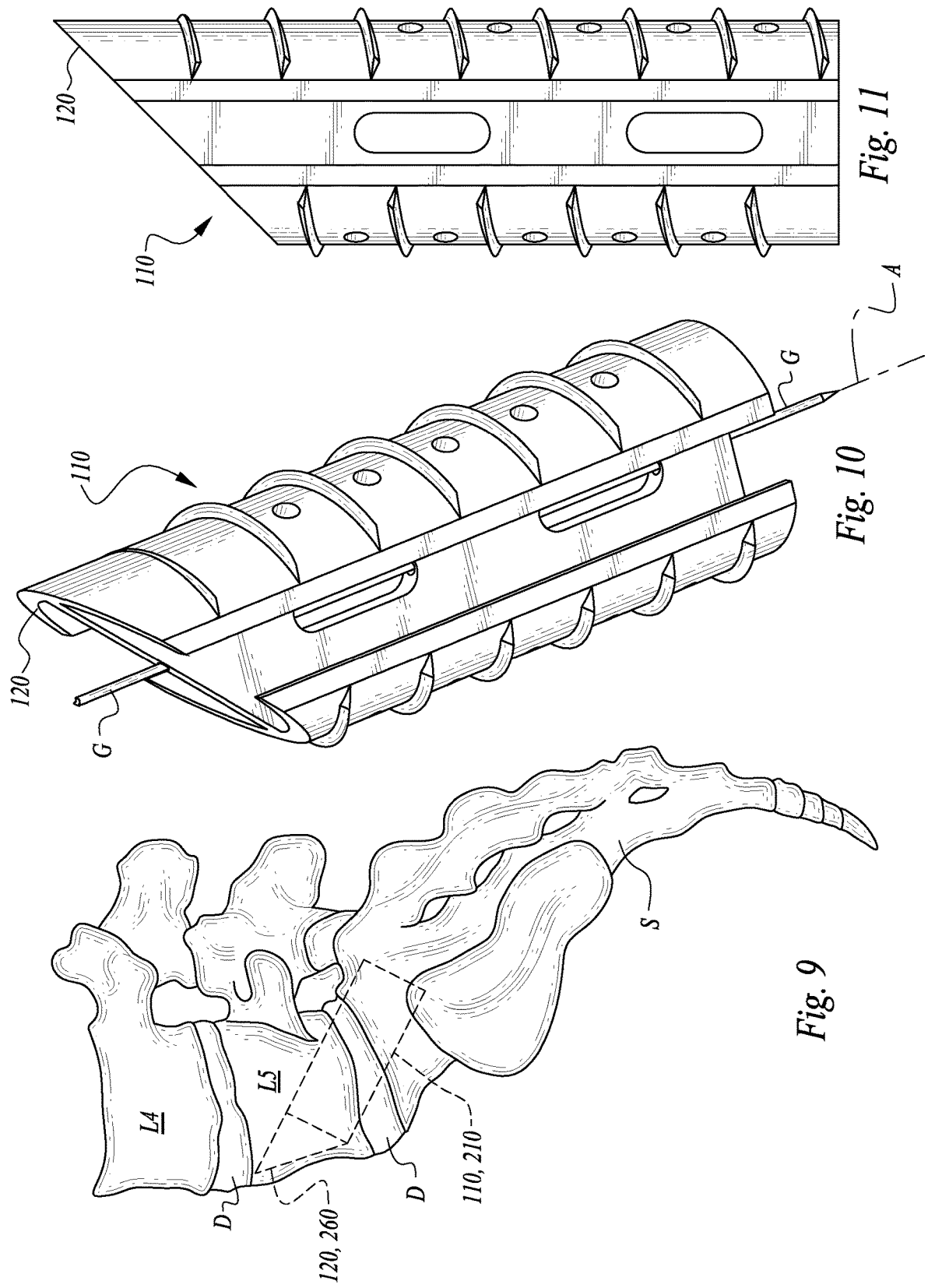
FIG. 9 is a side elevation view of a spine with a second or third alternative embodiment beam implant structure shown in broken lines at one position for implantation thereof.
FIG. 10 is a perspective view of the second alternative beam structure in the form of a tapered beam, and fitted upon a guide wire.
FIG. 11 is a side elevation view of that which is shown in FIG. 10.

With particular reference to FIGS. 9-11, details of an alternative embodiment tapered beam 110 are described. The tapered beam 110 is similar to the beam 10 of the preferred embodiment except that the trailing end 14 (or the leading end if the device is implanted in a posterior direction) is in the form of a tapered end 120. This tapered end 120 is not perpendicular to the central axis A of the tapered beam 110, but rather is angled, such as at 45° to the central axis A. This taper is preferably provided so that the web is also caused to be tapered at this tapered end 120 and so that one of the shells is generally longer than the other shell at the tapered end 120.

As particularly seen in FIG. 9, such a tapered beam 110 provides additional structural support within the L5 vertebra or other first vertebra above the disk space D for additional support of the vertebrae adjacent the disk space for maximum stabilization of the spine while fusing the vertebrae together.

Figures 12, 13:
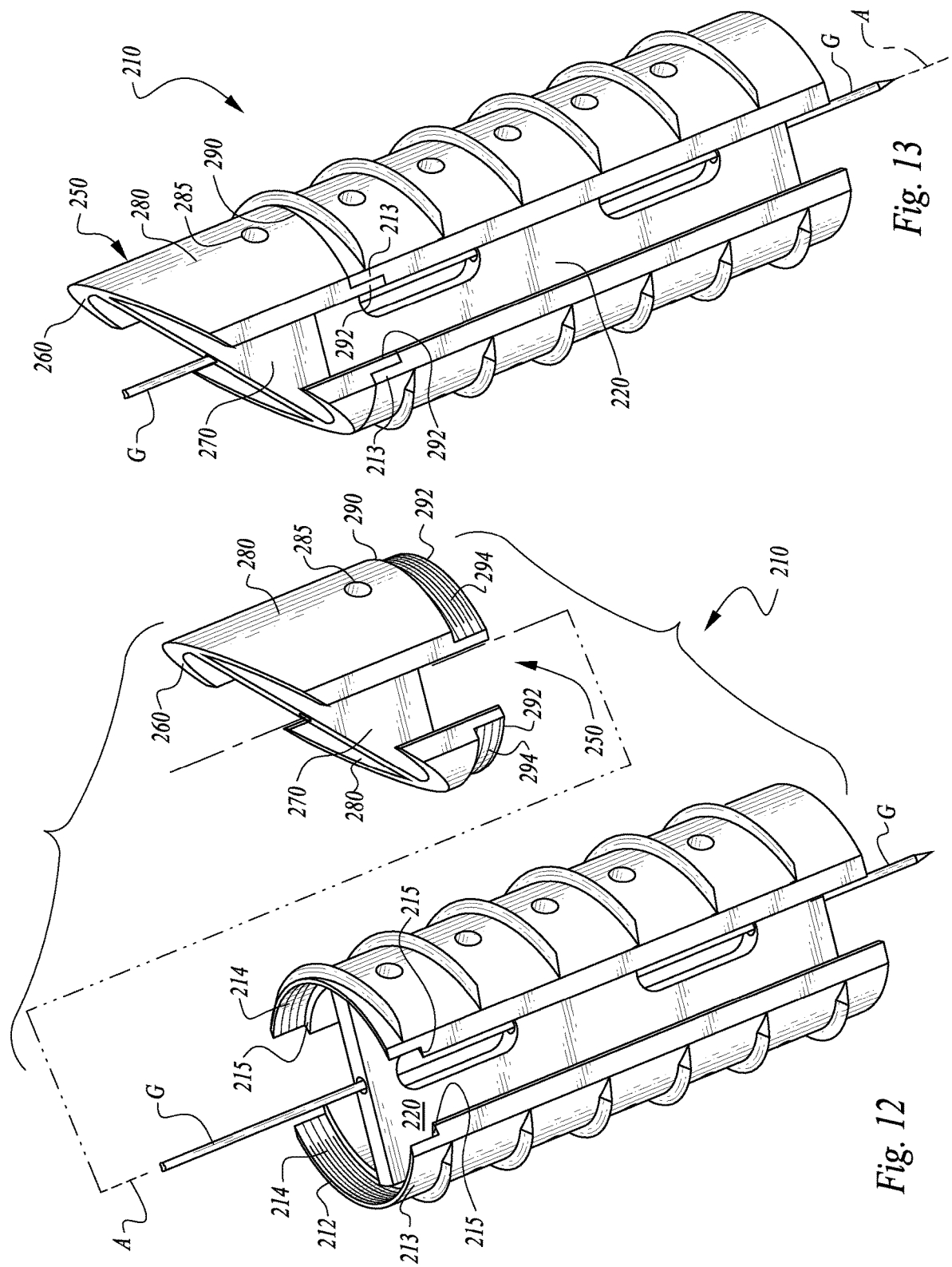
FIG. 12 is an exploded parts view of a third alternative embodiment beam structure in the form of a two-part beam structure including an extendible beam and an extension.
FIG. 13 is a perspective view similar to that which is shown in FIG. 12 but with the extension and extendible beam shown joined together.

With particular reference to FIGS. 12 and 13, a further beam 210 embodiment is shown similar to the tapered beam 110 but provided in two parts including the extendible beam 210 and the extension 250. The extendible beam 210 is similar to the beam 10 of the preferred embodiment with a generally cylindrical form with ends that are generally perpendicular to the central axis A. The extendible beam 210 differs from the beam 10 in that the trailing end is preferably configured as a threaded end 212 with internally facing female threads referred to as inner threads 214, formed on a cylindrical wall 213 at the threaded end 212. This threaded end 212 is formed by making the walls of the shells thinner at this cylindrical wall 213 and with the inner threads 214 extending radially in towards a central axis A.

A stop 215 defines where the cylindrical wall 213 transitions into the thicker wall of the shell. The web is preferably formed as a truncated web 220 which does not extend all the way to the cylindrical wall 213, but rather stops short so that a gap is provided between the truncated web 220 and the cylindrical wall 213.

A separate part is provided in the form of the extension 250. This extension 250 is generally cylindrical in form and includes a tapered end 260 opposite an attachment end 290. The tapered end 260 has a surface which is non-perpendicular and non-parallel with the central axis A, preferably with an angle such as 45° away from the central axis A. This tapered end 260 is thus similar to the tapered end 120 of the tapered beam 110 (FIGS. 9-11).

The extension 250 also includes a web 270 joining two shells 280 together and with holes 285 in the shells 280. The web 270 and shells 280 are similar to the web 20 and shells 30 of the beam 10 of the first embodiment, except that these structures extend axially along the central axis A a significantly shorter distance than that of the beam 10.

An attachment end 290 is provided opposite the tapered end 260. This attachment end 290 is preferably perpendicular to the central axis A and includes a cylindrical tab 292 extending axially somewhat from the attached end 290. This cylindrical tab 292 has a diameter slightly less than that of other portions of the shells 280 of the extension 250. Outer threads 294 are formed on the cylindrical tab 292 extending outwardly from the cylindrical tab 292. These outer threads 294 have a size and pitch which matches that of the inner threads 214 on the threaded end 212 of the extendible beam 210. Thus, the extension 250 can be threadably attached to the extendible beam 210 with such threading continuing until the attachment end 290 abuts the stop 215 at the threaded end 212 of the extendible beam 210.

The outer threads 294 and inner threads 214 are positioned so that the attachment end 290 of the extension 250 abuts the stop 215 of the threaded end 212 of the extendible beam 210 when the web 270 of the extension 250 is aligned in a common plane with the web of the extendible beam 210. The web 270 of the extension 250 preferably includes a bore passing therethrough that can be aligned with the extendible beam 210 through utilization of the guide wire G, extending along the central axis A. Once the extension 250 has been attached to the extendible beam 210, the completed extendible beam 210 is similar in form to the tapered beam 110.

Extensions 250 are preferably provided in a set having different characteristics. For instance, an axial length of different extensions 250 can differ. In this way, a surgeon can select an extension 250 having a desired length to maximize a length of the extendible beam 210 while still remaining generally within the outline of the vertebrae to be fused. If the extension 250 is attached to the extendible beam 210 and it is seen that the extension 250 is too short or too long in an axial direction, the extension 250 can be removed and replaced with an extension 250 having more desirable length characteristics. Furthermore, an angle of the tapered end 260 can vary for different extensions 250 within the set of extensions 250. For instance, if an angle diverging 30° away from perpendicular to central axis A would best remain within the general outline of the vertebrae to be fused, such an extension 250 can be selected.

Figure 1:
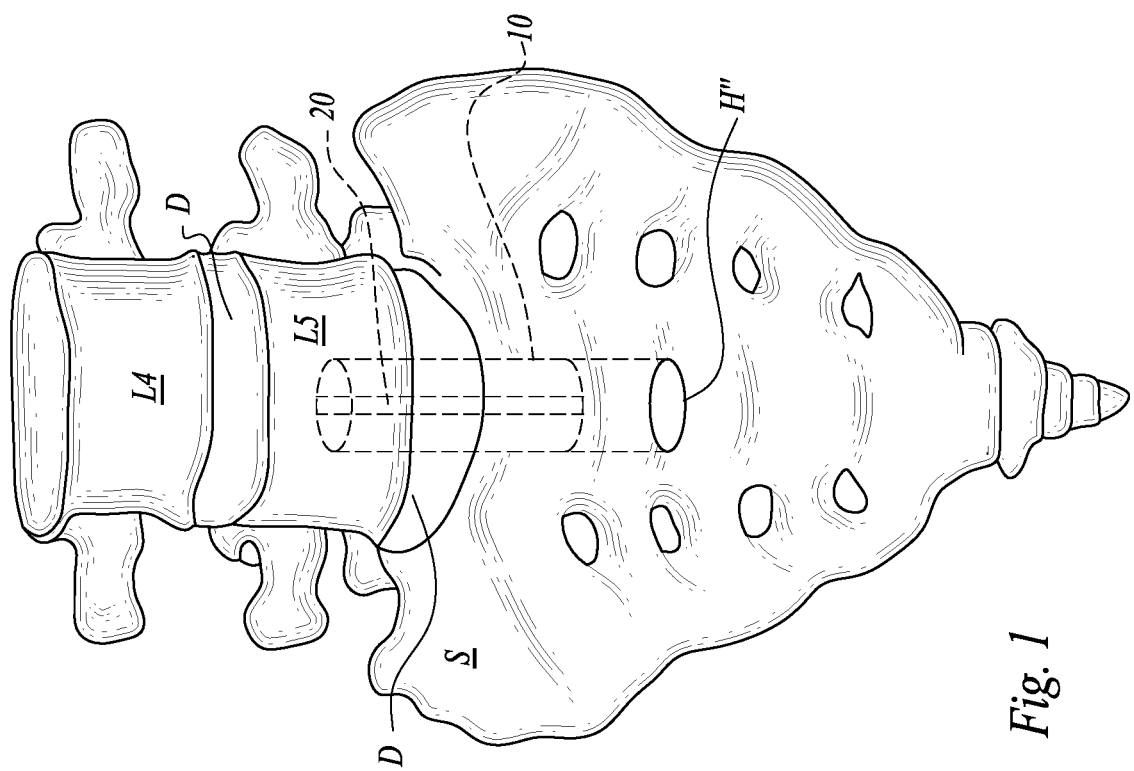
FIG. 1 is a front elevation view of a portion of the lower spine of a patient and with a beam implant of this invention shown in broken lines where it would be implanted into the spine of the patient.

In use and operation, and with particular reference to FIGS. 1, 2 and 9, details of the method of implantation of beams such as the beam 10, tapered beam 110 or extendible beam 210 are described. While these beams 10, 110, 210 could be implanted either posteriorly into a hole H" (FIG. 1) or anteriorly into a hole H' (FIG. 2), this particular method disclosed herein relates to an anterior method for beam 10, 110, 210 implantation.

Initially, an incision site is located and an incision is made. The procedure is preferably performed endoscopically or laparoscopically, and most preferably in the form of a mini-laparatomy. In particular, a cannula can be routed from the incision site to the first vertebra above the disk space to be crossed by the beam 10, 110, 210 and fused. In this example, this first vertebra is the L5 vertebra above the sacrum S.

A guide wire G is routed through the cannula and to the surface of the L5 vertebra or other first vertebra. The guide wire G is then routed through this first vertebra generally in a diagonal direction that is both posterior and distal, while remaining within a vertically central plane of the spine. The guide wire G can be guided through the assistance of fluoroscopy or other imaging techniques so that the surgeon can precisely place the guide wire G where desired.

Preferably, the guide wire G extends substantially linearly through the first vertebra. It preferably penetrates the first vertebra near an upper anterior edge of the vertebra and then passing through a caudal surface of the vertebra above the disk space D, passing through the disk space D diagonally, and then into the upper surface of the sacrum S. The guide wire G then continues diagonally into the sacrum S a distance desired for the beam 10, 110, 210, and preferably a small additional amount, so that the guide wire G can remain anchored within the sacrum S or other second vertebra for a remainder of the surgical procedure.

Next, bone cutting tools are routed along the guide wire G and through the cannula. These tools can include power or hand drills, reamers and other equipment for forming a cylindrical hole H' about a central axis aligned with the guide wire G. Preferably, this cylindrical hole H' forming process occurs in stages with each stage cutting an additional amount of bone away. The bone removed during this hole H' forming procedure is collected for later use in the bone fusion procedure.

After the cylindrical hole H' has been completely formed, the guide wire G remains passing through a central line of this cylindrical hole H'. This cylindrical hole H' passes entirely through the first vertebra, spans the disk space and extends in the form of a blind bore into the sacrum S or other second vertebra. As an alternative, this hole H″ could pass entirely through the sacrum S, but would require in most instances retraction of nerves to avoid impacting nerves passing through portions of the sacrum S. In a posterior procedure it can be seen that by retraction of appropriate nerves, the hole H″ could be formed from a posterior side and extending anteriorly through the sacrum S, spanning the disk space D and at least into the L5 vertebra and conceivably entirely through the L5 vertebra. Thus, a similar procedure can be utilized both for posterior or anterior formation of the cylindrical hole H. In the most preferred embodiment, the sacrum S is not entirely penetrated, so that the guide wire G can remain anchored within a portion of the sacrum S just past the cylindrical hole H′.

A tapping instrument can then be utilized to tap the cylindrical hole H′ if desired. If differential threads are to be utilized, typically only the first vertebra is tapped. If the beam 10, 110, 210 is to have a stepped configuration with a lesser diameter adjacent the leading end 12 and a greater diameter adjacent the trailing end 14, the cylindrical hole H′ is formed to match this contour with a lesser diameter in the sacrum S and a greater diameter passing through the L5 vertebra or other first vertebra. With such a stepped configuration, the entire cylindrical hole H′ can be tapped, even if differential threads are to be utilized, and tapping tools for tapping the threads having different pitches are utilized for the different portions of the cylindrical hole H′ on opposite sides of the step.

Next, the beam 10, 110, 210 is routed over the guide wire G, from the incision site through the cannula and into the cylindrical hole H′. If a tapered beam 110 or extendible beam 210 is utilized, the tapered end 110 or threaded end 212 is oriented at the trailing end as the beam 10, 110, 210 is routed along the guide wire G and into the cylindrical hole H′ within the spine. Once the beam 10 has reached the first vertebra, it is further advanced by rotation of the beam 10 with engagement of the threads 40 with female threads within the cylindrical hole H′ to advance the beam 10 entirely into the hole H′ and filling the cylindrical hole H′, with the beam 10, 110, 210 spanning the disk space D.

The disk space D can have the disk removed therefrom in a preliminary procedure or the disk space D can really be penetrated with the remnants of the disk remaining in place, or with the disk removed, or at least a nucleus of the disk removed during the formation of the cylindrical hole during the drilling or reaming procedures described above.

When the beam 10, 110, 210 has advanced substantially entirely into the hole H′, it is important that the beam 10 finish with the web 20 remaining within a vertical plane bisecting the spine to provide maximum strength to the beam 10. This might require the beam 10, 110, 210 stopping slightly short of abutting against a circular end wall in the cylindrical hole H′. If the beam 10 is in the form of the tapered beam 110, alignment of the web 20 also causes alignment of the tapered end 120 as desired.

If the extendible beam 210 is initially implanted, a further step is provided where an extension 250 is selected having a desired axial length and then advanced along the guide wire G and then threadably attached to the threaded end 212 of the extendible beam 210 to complete the extendible beam 210 (FIG. 13).

Finally, bone matter scavenged during the drilling and/or reaming process, as well as the tapping process, are passed through the cannula and into space inside of the shells 30 of the beam 10 and into the disk space. Further in-growth media is also packed into the space and other preparations known in the art are completed to encourage bone in-growth and to complete fusion of the first vertebra to the second vertebra spanning the disk space D. Holes 35 in the beam 10 and apertures 26 in the web 20 allow for bone in-growth through the shells 30 and web 20. These holes 35 can be sized larger or smaller to optimize such bone in-growth while still maintaining strength, and can either be circular or have other contours.

After the beam 10, 110, 210 has been placed entirely where desired, the guide wire G can be removed from the beam 10 at an end of the procedure. Finally, the cannula can be removed and the incision site closed to complete the spinal fusion procedure.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A method for fusing two vertebrae together, including the steps of:
   boring a substantially cylindrical hole through a first vertebrae, through a disk space and at least into a second vertebrae on a side of the disk space opposite the first vertebrae;
   providing an implantable structure having an elongate form extending from a leading end to a trailing end, the structure having a generally cylindrical outer contour adapted to be routed axially into the hole formed in the first and second vertebrae, the structure including a central web, the structure including at least two shells forming at least a portion of the outer contour of the structure, and the web joining the two shells together the at least two shells each having a semi-cylindrical contour, the at least two shells each extending from the leading end to the trailing end of the structure, the shells spaced from adjacent shells by gaps; and
   inserting the structure into the hole of said boring step with the structure spanning the disk space and extending at least partially into the first vertebrae and at least partially into the second vertebrae.

2. The method of claim 1 including the further step of encouraging fusion of the first vertebrae with the second vertebrae and to the implantable structure.

3. The method of claim 1 wherein said boring step includes the step of placing a guide wire along a path desired for the bore and providing a bone boring tool adapted to follow a guide wire and utilizing the bone boring tool to form at least a portion of the hole through the first and second vertebrae according to said boring step.

4. The method of claim 3 wherein said inserting step includes the step of keeping the guide wire of said boring step in after said boring step and routing the implantable structure over the guide wire within the hole to place the structure within the hole formed in the first and second vertebrae.

5. The method of claim 4 wherein said web includes an axial bore passing therethrough sized sufficiently large to receive the guide wire therein.

6. The method of claim 1 including the further step of providing threads on the implantable structure of said providing step, said threads being self-tapping in nature.

7. The method of claim 1 including the further steps of:
said providing step including the implantable structure having male threads on an outer surface of the implantable structure; and
tapping the hole of said boring step with a thread tapping instrument separate from the implantable structure, to form female threads adapted to receive the male threads on the implantable structure of said providing step.

8. The method of claim 1 wherein at least one of said ends of said structure is adapted to be coupled to an extension, said extension formed of rigid material, said extension having a first end adapted to be attached to the implantable structure and a second end with a flat surface oriented at an angle tapered to be neither perpendicular nor parallel with a central axis of the implantable structure.

9. The method of claim 8 including the further steps of:
forming at least one surface of the extension to have a flat surface which is tapered;
selecting an extension having a length and taper angle desired; and
attaching the extension of said selecting step to the implantable structure to extend a length of the implantable structure.

10. The method of claim 1 wherein said providing step includes the gaps between adjacent ones of the shells extending from the leading edge to the trailing edge of the structure.

11. The method of claim 1 wherein said providing step includes the web having a planar form extending from the leading edge to the trailing edge.

12. The method of claim 11 wherein said providing step includes the web joined to each of the at least two shells at junctions spaced from the gaps.

13. A method for fusing two vertebrae together, including the steps of:
boring a substantially cylindrical hole through a first vertebrae, through a disk space and at least into a second vertebrae on a side of the disk space opposite the first vertebrae;
inserting into the cylindrical hole of said boring step an implantable structure having an elongate form extending from a leading end to a trailing end, the structure having a generally cylindrical outer contour adapted to be routed axially into the hole formed in the first and second vertebrae, the structure including a central web, the structure including at least two shells forming at least a portion of the outer contour of the structure, and the web joining the two shells together the at least two shells each having a semi-cylindrical contour, the at least two shells each extending from the leading end to the trailing end of the structure, the shells spaced from adjacent shells by gaps; and
said inserting step orienting the structure spanning the disk space and extending at least partially into the first vertebrae and at least partially into the second vertebrae.

14. The method of claim 13 including the further step of encouraging fusion of the first vertebrae with the second vertebrae and to the implantable structure.

15. The method of claim 13 wherein said boring step includes the step of placing a guide wire along a path desired for the bore and providing a bone boring tool adapted to follow a guide wire and utilizing the bone boring tool to form at least a portion of the hole through the first and second vertebrae according to said boring step.

16. The method of claim 15 wherein said inserting step includes the step of keeping the guide wire of said boring step in after said boring step and routing the implantable structure over the guide wire within the hole to place the structure within the hole formed in the first and second vertebrae.

17. The method of claim 13 wherein at least one of said ends of said structure is adapted to be coupled to an extension, said extension formed of rigid material, said extension having a first end adapted to be attached to the implantable structure and a second end with a flat surface oriented at an angle tapered to be neither perpendicular nor parallel with a central axis of the implantable structure;
selecting an extension having a length and taper angle desired; and
attaching the extension of said selecting step to the implantable structure to extend a length of the implantable structure.

18. The method of claim 10 wherein said providing step includes the gaps between adjacent ones of the shells extending from the leading edge to the trailing edge of the structure.

19. The method of claim 13 wherein said providing step includes the web having a planar form extending from the leading edge to the trailing edge.

20. The method of claim 13 wherein said providing step includes the web joined to each of the at least two shells at junctions spaced from the gaps.

* * * * *